United States Patent
Kanazawa et al.

(10) Patent No.: US 12,298,988 B2
(45) Date of Patent: May 13, 2025

(54) SERVER AND INFORMATION PROCESSING METHOD FOR COLLECTING HUMAN VITAL DATA AND PROVIDING THE DATA TO USERS

(71) Applicant: FIRST SCREENING CO., LTD., Tokyo (JP)

(72) Inventors: Yohei Kanazawa, Tokyo (JP); Yoshito Tsunoda, Tokyo (JP)

(73) Assignee: FIRST SCREENING CO., LTD. (JP)

( * ) Notice: Subject to any disclaimer, the term of this patent is extended or adjusted under 35 U.S.C. 154(b) by 56 days.

(21) Appl. No.: 17/312,434

(22) PCT Filed: Dec. 11, 2018

(86) PCT No.: PCT/JP2018/045514
§ 371 (c)(1),
(2) Date: Jun. 10, 2021

(87) PCT Pub. No.: WO2020/121409
PCT Pub. Date: Jun. 18, 2020

(65) Prior Publication Data
US 2022/0019583 A1 Jan. 20, 2022

(51) Int. Cl.
*G06F 16/00* (2019.01)
*G06F 16/22* (2019.01)
(Continued)

(52) U.S. Cl.
CPC ...... *G06F 16/2477* (2019.01); *G06F 16/2272* (2019.01); *G06F 16/24565* (2019.01); *G06F 16/258* (2019.01); *G06F 16/285* (2019.01)

(58) Field of Classification Search
None
See application file for complete search history.

(56) References Cited

U.S. PATENT DOCUMENTS 6,003,029 A * 12/1999 Agrawal ............... G06F 18/23
8,108,397 B2 * 1/2012 Kawai ............... G06F 16/1748
707/822

(Continued)

FOREIGN PATENT DOCUMENTS

JP 2000-312666 A 11/2000
JP 2005-293026 A 10/2005
(Continued)

OTHER PUBLICATIONS

International Search Report (English and Japanese) of the International Searching Authority issued in PCT/JP2018/045514, mailed Mar. 19, 2019; ISA/JP (4 pages).

(Continued)

*Primary Examiner* — Farhan M Syed
(74) *Attorney, Agent, or Firm* — Harness, Dickey & Pierce, P.L.C.

(57) ABSTRACT

A server receives a first type of time-series vital data from a first system that collects the first type of time-series vital data from a first group of subjects, and receives a second type of time-series vital data from a second system that collects a second type of time-series vital data from a second group of subjects. Provided are a storage unit for storing a plurality of types of time-series vital data including the first type and the second type, a receiving unit for receiving a request for provision of the time-series vital data from an external device that specifies at least a part of the time-series vital data stored in a vital data database, and a transmitting means for transmitting to the external device the time-series vital data selected in accordance with a request for provision from among the time-series vital data stored in the vital data database.

20 Claims, 5 Drawing Sheets

(51) Int. Cl.
*G06F 16/2455* (2019.01)
*G06F 16/2458* (2019.01)
*G06F 16/25* (2019.01)
*G06F 16/28* (2019.01)

(56) References Cited

U.S. PATENT DOCUMENTS

| | | | | |
|---|---|---|---|---|
| 10,169,720 | B2* | 1/2019 | Chien | G06F 16/285 |
| 10,474,968 | B2* | 11/2019 | Chien | G06N 20/00 |
| 11,561,273 | B2* | 1/2023 | Ohyu | G01R 33/5601 |
| 2005/0215868 | A1 | 9/2005 | Kenjou et al. | |
| 2008/0319951 | A1* | 12/2008 | Ueno | G06F 16/285 |
| | | | | 707/E17.046 |
| 2010/0042624 | A1* | 2/2010 | Min | G06F 16/285 |
| 2014/0229349 | A1 | 8/2014 | Yanev et al. | |
| 2017/0017764 | A1* | 1/2017 | Tsugo | G16H 40/63 |
| 2017/0228661 | A1* | 8/2017 | Chien | G06F 16/285 |
| 2018/0102938 | A1* | 4/2018 | Yoon | G06F 16/358 |
| 2018/0203744 | A1* | 7/2018 | Wiesmaier | G06F 9/505 |
| 2019/0050473 | A1* | 2/2019 | Bhattacharya | G06F 16/285 |
| 2019/0108460 | A1* | 4/2019 | Chien | G06Q 10/063 |
| 2020/0125471 | A1* | 4/2020 | Garvey | G06F 18/217 |

FOREIGN PATENT DOCUMENTS

| | | |
|---|---|---|
| JP | 2005-305134 A | 11/2005 |
| JP | 2012-090784 A | 5/2012 |
| JP | 2016-511890 A | 4/2016 |
| JP | 2017-006649 A | 1/2017 |

OTHER PUBLICATIONS

Office Action issued in corresponding Japanese Application No. 2020-020056 dated Jan. 10, 2023, with English translation (7 Pages).

* cited by examiner

| IDENTIFICATION NUMBER | 967754B | | | |
|---|---|---|---|---|
| BLOOD PRESSURE | 120/71 2018/11/27 09:01 | 125/68 2018/11/28 09:15 | ... | 115/70 2018/11/30 08:32 |
| HEART RATE | 61 2018/11/27 09:01 | 57 2018/11/28 09:15 | ... | 59 2018/11/30 08:32 |
| BLOOD SUGAR | 92 2018/05/28 11:21 | — | — | — |
| URINARY SUGAR | (−) 2018/11/27 07:56 | (−) 2018/11/27 11:29 | ... | (−) 2018/11/27 18:52 |
| URINIC ACID | 4.1 2018/11/27 07:56 | 4.3 2018/11/27 11:29 | ... | 4.5 2018/11/27 18:52 |
| OXALIC ACID | 20.1 2018/11/27 07:56 | 25.9 2018/11/27 11:29 | ... | 22.2 2018/11/27 18:52 |
| PROPORTION | 1.011 2018/11/27 07:56 | 1.013 2018/11/27 11:29 | ... | 1.014 2018/11/27 18:52 |
| ... | ... | ... | ... | ... |
| PROTEIN | (−) 2018/11/27 07:56 | (−) 2018/11/27 11:29 | ... | (−) 2018/11/27 18:52 |

| COMMON IDENTIFICATION INFORMATION | IDENTIFICATION INFORMATION IN EXTERNAL SYSTEM 2 | IDENTIFICATION INFORMATION IN EXTERNAL SYSTEM 3 | ... |
|---|---|---|---|
| 967754B | ABC001 | 123456 | ... |
| 823467C | DEF209 | NA | ... |
| ... | ... | ... | ... |

SERVER AND INFORMATION PROCESSING METHOD FOR COLLECTING HUMAN VITAL DATA AND PROVIDING THE DATA TO USERS

CROSS REFERENCE TO RELATED APPLICATIONS

This application is a U.S. National Phase Application under 35 U.S.C. 371 of International Application No. PCT/JP2018/045514, filed on Dec. 11, 2018. The entire disclosure of the above application is expressly incorporated by reference herein.

BACKGROUND

Technical Field

The present invention relates to technology for providing vital data.

Related Art

Systems for collecting vital data are known. For example, JP 2000-312666 A discloses a system that changes a display layout for displaying data in response to contents of a vital sensor selected from among multiple vital data sensors and obtained from a user. JP 2005-293026 A also describes aggregating DICOM (Digital Imaging and Communications in Medicine) data, which is obtained from a plurality of measurement devices, into an integrated DICOM server to provide a search service.

The system described in JP 2000-312666 A is subject to a problem in that the system does not provide vital data acquired from plural subjects to other users. In addition, the system described in JP 2005-293026 A merely handles DICOM data, and is unable to handle a variety of vital data.

In contrast, the present disclosure provides a technology that collects a variety of vital data from multiple subjects and provides this data to other users.

SUMMARY

According to one aspect of the disclosure, there is provided a server including: an input receiving unit that receives input of a first type of time-series vital data from a first system for collecting the first type of time-series vital data from a first group of subjects; an identifying unit that identifies attribute data indicating an attribute of a subject at a time when the time-series vital data were measured, for time-series vital data that are a target among the time-series vital data input of which is received by the input receiving unit; a writing unit that writes the time-series vital data, the input of which is received by the input receiving unit, into a vital data database together with information indicating a correspondence relationship with the attribute data identified by the identifying unit; a clustering unit that clusters the time-series vital data recorded in the vital data database based on the attribute data; a request receiving unit that receives a request for providing data including classification information that specifies the classification by the clustering unit; an extracting unit that extracts the time-series vital data belonging to the cluster specified by the classification information from the vital data database; and an output unit that outputs the time-series vital data extracted by the extracting unit to a device specified by the request.

The vital data database may store the attribute data in a format that allows reference to changes in the attribute data over time.

The server may further include an estimation unit that estimates the attributes of the subject.

The output unit may transmit to the device, along with the extracted time-series vital data, classification information indicating clusters into which the time-series vital data are classified by the clustering unit.

The identifying unit may identify the attribute data based on links corresponding to the time-series vital data.

The request may include an authentication key to authenticate a device. The server may further include an authentication unit to authenticate the device using the authentication key included in the request, wherein when the device is authenticated by the authentication unit, the output unit outputs time-series vital data selected in accordance with the request.

The authentication key may include at least one of timestamps and measurements of at least two data points of time-series vital data previously acquired at the device; and the authentication unit may performs authentication by matching the authentication key with the time-series vital data stored in the vital data database.

If the number of data points in the time-series vital data included in the authentication key is less than a threshold value, the authentication key may include both the time stamps and the measurement values of the at least two data points, and if the number of data points in the time-series vital data included in the authentication key is greater than the threshold value, the authentication key may include only one of the timestamps and the measurement values of the at least two data points.

The authentication key may include index information for identifying data points from the group of time-series vital data stored by the device, and the authentication unit may perform the authentication by matching the authentication key with the data points identified by the index information among the time-series vital data stored in the vital data database.

The index information may include subject identification information that identifies one subject from among a plurality of subjects, and the authentication unit may perform the authentication by matching the authentication key with the data points included in the time-series vital data of the one subject from among the time-series vital data stored in the vital data database.

The input receiving unit may receive the input of the second type of time-series vital data from a second system that collects a second type of time-series vital data from a second group of subjects, the identifying unit may identify the attribute data indicating the attribute of the subject at the time when the time-series vital data was measured, for the time-series vital data that is the subject among the second type of time-series vital data, and the writing unit may write the second type time-series vital data to the vital data database together with information indicating the correspondence with the attribute data identified by the identifying unit.

The server may further include a conversion unit that converts individual identification information into common identification information commonly used in the vital data database if the time-series vital data received by the input receiving unit include individual identification information that identifies the subject of the time-series vital data, the individual identification information being individually assigned in the first system or the second system, wherein the vital data database may store the common identification information as information to identify the subject.

The clustering unit may classify the second type of time-series vital data based on the first type of time-series vital data from among multiple types of time-series vital data.

The input receiving unit may receive vital data written in a first format from the first system, and receives vital data written in a second format from the second system, the vital data database may store the first rule for converting the vital data in the first format to the vital data in a standard format, and the second rule for converting the vital data in the second format to the vital data in the standard format, and the writing unit may write the data converted from the vital data received by the input receiving unit to the standard format to the vital database.

The vital data database may store multiple types of time-series vital data, the request may include information to select at least some of the multiple types, and the output unit may transmit to the device the type of vital data selected in accordance with the request, the type of vital data being selected from among the vital data of all subject groups including the first and second subject groups, the vital data being stored in the vital data database.

The request may include time period information to narrow down a time period, the output unit may transmits to the device vital data measured during a limited time period in accordance with the request, the transmitted vital data being selected from the time-series vital data stored in the vital database.

The server may further include a calculation unit that calculates a charge for the time-series vital data received by the input receiving unit.

Constraint conditions on a time axis to be satisfied by the time-series vital data are set, and the charge calculation unit calculates the charge in accordance with a percentage of the data received by the input receiving unit that satisfies constraint conditions.

According to another aspect of the disclosure, there is provided an information processing method including: receiving an input of a first type of time-series vital data from a first system that collects the first type time-series vital data from a first group of subjects; identifying attribute data indicating an attribute of a subject at a time when the time-series vital data was measured, for the time-series vital data that is a target among the time-series vital data for which the input was received; writing the input time-series vital data into the vital database, together with information indicating a correspondence with the identified attribute data; clustering the time-series vital data recorded in the vital data database based on the attribute data; receiving a request to provide data, the request including classification information specifying a classification by the clustering; extracting the time-series vital data belonging to a cluster specified by the classification information from the vital database; and outputting the extracted time-series vital data to the device specified by the request.

According to yet another aspect of the invention, there is provided a program causing a computer to execute a process, the process including: receiving an input of a first type of time-series vital data from a first system that collects the first type time-series vital data from a first group of subjects; identifying attribute data indicating an attribute of a subject at a time when the time-series vital data was measured, for the time-series vital data that is the target among the time-series vital data for which the input was received; writing the input time-series vital data into the vital database, together with information indicating a correspondence with the identified attribute data; clustering the time-series vital data recorded in the vital data database based on the attribute data; receiving a request to provide data, the request including classification information specifying a classification by the clustering; extracting the time-series vital data belonging to a cluster specified by the classification information from the vital database; and outputting the extracted time-series vital data to the device specified by the request.

DETAILED DESCRIPTION

1. Configuration

Figure 1:
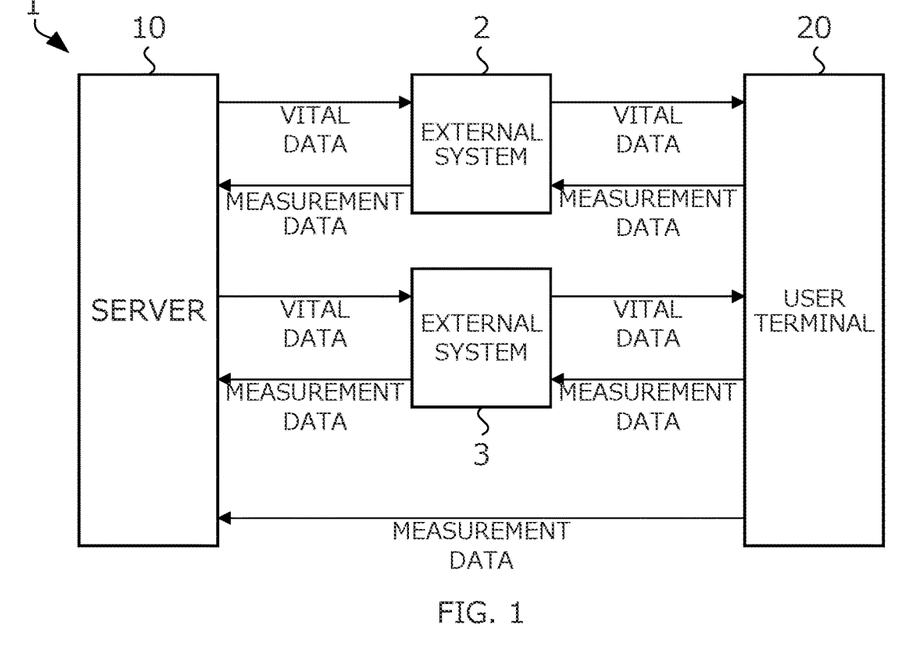
FIG. 1 shows an overview of the vital data providing system 1 according to one embodiment.

FIG. 1 shows an overview of a vital data providing system 1 according to one embodiment. The vital data providing system 1 is a system for providing vital data. The term "vital data" refers to data that can be obtained from a human body, such as at least one of blood pressure, heart rate, body temperature, oxygen saturation concentration (blood oxygen), body weight, blood glucose, urine glucose, uric acid (in blood or urine), oxalic acid, specific gravity, protein, urobilinogen (liver system), pH, serum iron, inflammation markers, creatinine, cholesterol ketones, cancer markers, H. pylori, steps, pulse, acceleration, location, calories consumed, outside temperature, outside humidity, and amount of sleep. The vital data includes, for example, information obtained from human body fluids (e.g., urine, sweat, or blood). In addition, the term "time-series vital data" refers to vita data that is recorded in a time series.

The vital data providing system 1 includes an external system 2, an external system 3, a server 10, and a user terminal 20. The vital data providing system 1 is a system that provides time-series vital data provided by the external system 2 and the external system 3 to other devices upon request. The other devices to which the time-series vital data are provided are, for example, other external systems or the user terminals 20. In this example, the server 10, the external system 2, and the external system 3 are each operated by a different operator Although for convenience of illustration only two external systems and one client are shown in the drawings, the vital data providing system 1 may have three or more external systems and two or more clients.

The external system 2 is an example of a first system that collects a first type of time-series vital data from a first group of subjects. The external system 3 is an example of a second system that collects a second type of time-series vital data from a second group of subjects. The first subject group and the second subject group are each subject groups that include plural subjects and the first and the second subject group are at least partially different from each other. Each of the first type time-series vital data and the second type time-series vital data constitute one or more types of time-series vital data and the first and second types of time-series vital data are at least partially different are at least partially different. For example, the external system 2 is a system operated by a hospital, and the time-series vital data collected by the external system 2 includes, for example, blood pressure, heart rate, body temperature, oxygen saturation concentration (blood oxygen), and body weight. The time-series vital data collected by the external system 3 includes, for example, blood glucose, urine glucose, uric acid (in blood or urine), oxalic acid, specific gravity, and protein. In addition, a gym, for example, may operate an external system, and in this case, the time-series vital data collected by this external system include, for example, steps, pulse, acceleration, position, and calories consumed.

Figure 2:
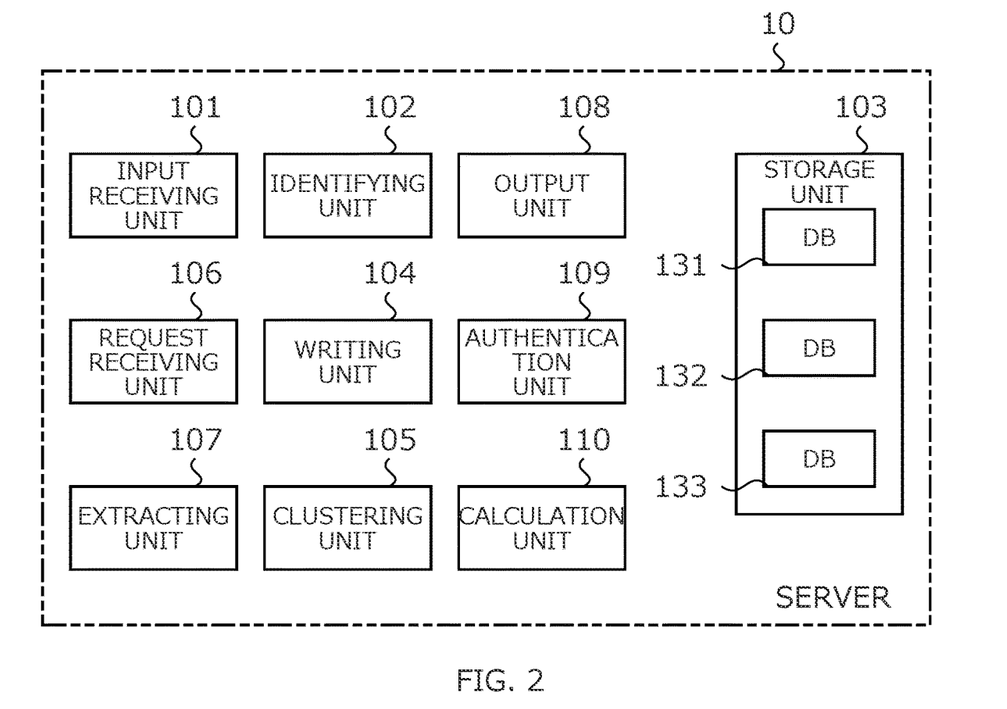
FIG. 2 illustrates an exemplary functional structure of the server 10.

FIG. 2 illustrates an exemplary functional structure of the server 10. The server 10 has a receiving unit 101, an identifying unit 102, a storage unit 103, a writing unit 104, a clustering unit 105, a receiving unit 106, an extracting unit 107, and an output unit 108.

The receiving unit 101 receives input of time-series vital data from an external system. The data received by the receiving unit 101 include at least one of the first type time-series vital data collected by the external system 2 and the second type time-series vital data collected by the external system 3. The identifying unit 102 identifies, with respect to the time-series vital data that are the target of the time-series vital data input of which is received by the receiving unit 101, data indicating attributes of a target subject at a time when the time-series vital data is measured as attribute data thereof. The storage unit 103 stores various types of data. The database stored by the storage unit 103 include(s), for example, a vital data database 131, an attribute database 132, and an identity database 133 (denoted simply as DB 131, DB 132, and DB 133 in the figures). The attribute database 132 includes the vital data database 131. The vital data database 131 is a database that records time-series vital data for which input is received by receiving unit 101. The attribute database 132 is a database that records the attributes of the subjects. The attributes of the subjects are classified into those that are non-time-variable and those that are time-variable. The non-time-variable attributes include, for example, gender, date of birth, place of birth, and race. The time-variable attributes include, for example, age group, pre-existing medical conditions, smoking history, alcohol intake history, exercise history, residential area, and average sleep time. The identity database 133 is a database used to register the names of subjects. The writing unit 104 writes an item of the time-series vital data input of which is received by the receiving unit 101 to the vital data database, together with information indicating a correspondence with the attribute data identified by the identifying unit 102.

Figure 3:
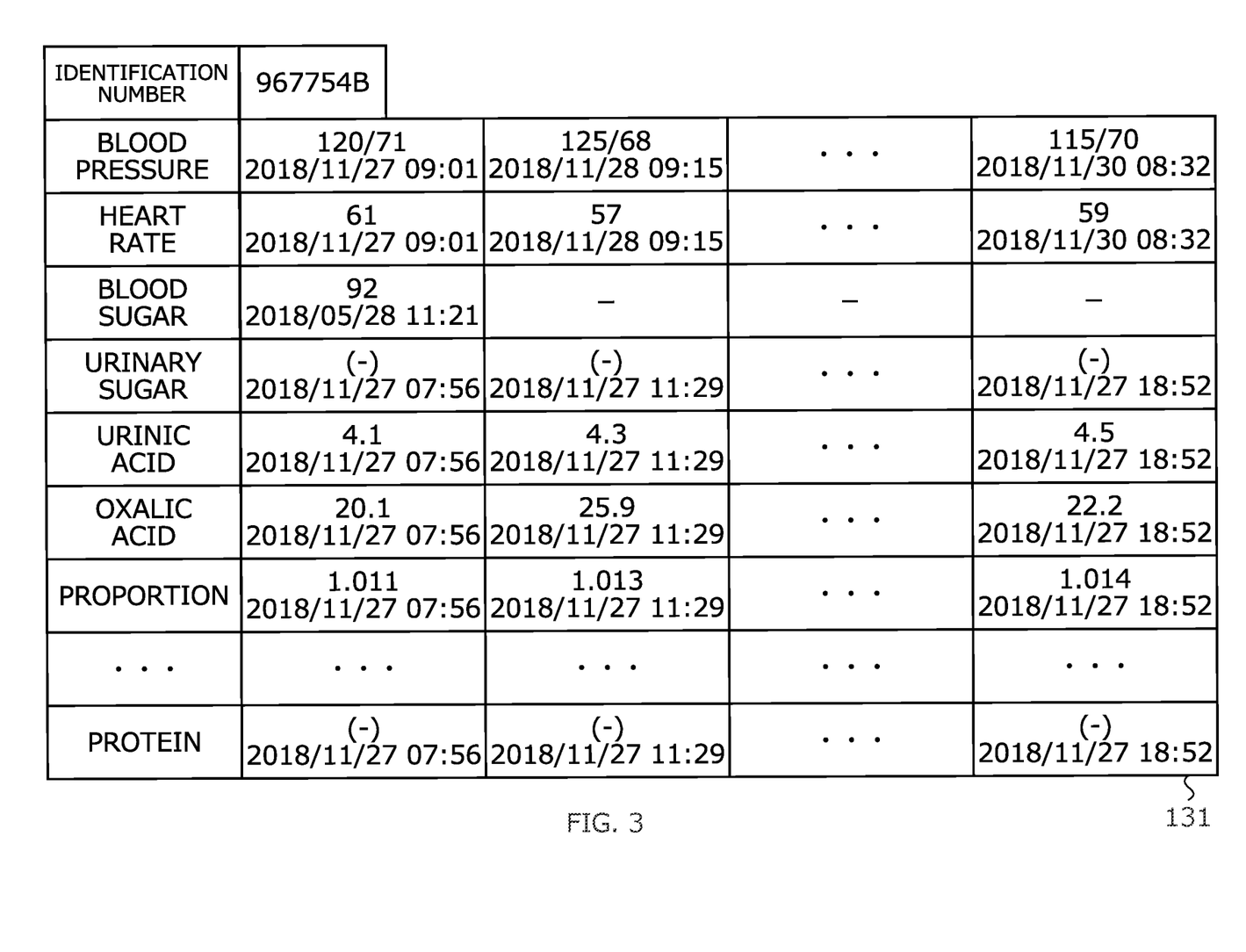
FIG. 3 shows an overview of the vital data database 131.

FIG. 3 shows an overview of the vital data database 131. Here, for clarification, the vital data database 131 is represented by a matrix, where one matrix represents vital data obtained from a single subject. In this example, the vital data database 131 does not include any personal information. The term "personal information" refers to information that could be used to identify a specific individual, such as at least one of a person's name, address, "my number" (social security number), telephone number, email address, and the mother's maiden name. In this matrix, each row represents a time-series change in a certain type of vital data. Each column shows a measured value for each of vital data. Here, for simplicity of explanation, an example where a single measurement is stored in each cell of the matrix is described. In addition to the measured value of the vital data, each cell also includes a time stamp related to the measured value. The timestamp indicates a time when the vital data were measured or when the vital data were acquired. In this example, the measured values belonging to a certain column are not necessarily values obtained by the measurement in the same time period. For example, the heartbeat in column 2 is a measurement taken at 9:15 am on Nov. 28, 2018, while the urine glucose in column 2 is a measurement taken at 11:29 am on Nov. 27, 2018. The matrix in FIG. 2 is recorded for each subject. In the vital data database 131, each subject is distinguished, for example, by an identification number allocated by the vital data providing system 1. Details of the vital data database 131 will be described later.

The description refers to FIG. 2 again. The clustering unit 105 clusters the time-series vital data recorded in the vital data database 131 based on the attribute data.

The receiving unit 106 receives a request for provision of data from an external system. This provision request includes information (hereinafter, "classification information") that specifies a cluster (classification) obtained as a result of clustering by the clustering unit 105. The extracting unit 107 extracts from the vital data database 131 the time-series vital data belonging to the cluster specified by the classification information. The output unit 108 outputs the time-series vital data extracted by the extracting unit 107 to a device specified in a provision request. In one example, the device designated by the provision request is the device that is the source of the provision request.

The receiving unit 106 receives a request for the provision of time-series vital data (hereinafter, "provision request") from another device. The provision request is sent from the external system 2, the external system 3, or the user terminal 20. The provision request includes information that specifies at least a part of the time-series vital data stored in the storage unit 103. This information includes, for example, information specifying clusters obtained by the clustering unit 105 (hereinafter, "classification information").

In this example, the server 10 further includes an authentication unit 109 and a charge calculation unit 110. The authentication unit 109 authenticates a request from another device such as the user terminal 20. If the request is authenticated, the extracting unit 107 extracts the data specified by the provision request from the vital data database 131. The output unit 108 transmits the extracted data to the device that is the source of the provision request (hereinafter, "source device") or the device specified by the provision request. If the request is not authenticated, the output unit 108 does not transmit the time-series vital data specified by the authentication request to the source device or the like.

The charge calculation unit 110 calculates a charge to be paid for the time-series vital data received by the receiving unit 101. The operator of the server 10 pays fees to the provider of the time-series vital data (e.g., the operator of the external system 2 and the external system 3, or each subject) for providing the time-series vital data. The charge calculation unit 110 calculates the fee amount to be charged.

The description refers to FIG. 1 again. The user terminal 20 is an information processing device for accessing at least one of the server 10, the external system 2, and the external system 3. The user terminal 20 is used, for example, by an end user. The end user is, for example, a subject. The subject is a person who provides his/her own time-series vital data to the vital data providing system 1. The user terminal 20 transmits a provision request that includes information that identifies the device or the subject, for example, to the external system 2. The external system 2 sends the data corresponding to this provision request to the user terminal 20. Although only one user terminal 20 is shown in detail in FIG. 1, multiple user terminals 20, each used by different subjects, can access at least one of the server 10, the external system 2, and the external system 3.

Figure 4:
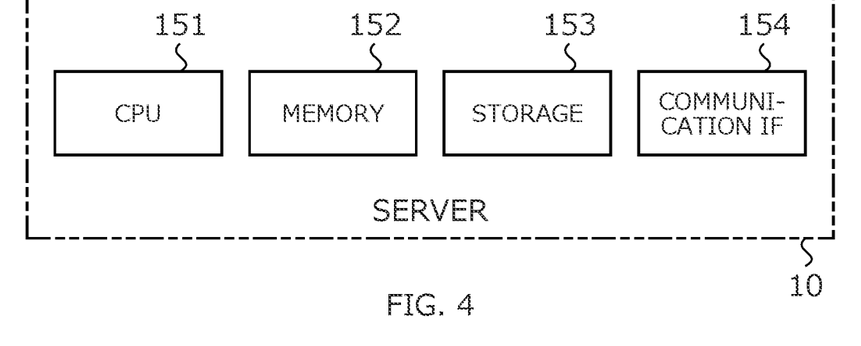
FIG. 4 illustrates an exemplary hardware configuration of the server 10.

FIG. 4 illustrates an exemplary hardware configuration of the server 10. The server 10 is a computer device having a CPU 151, a memory 152, a storage 153, and a communication IF 154. The CPU 151 is a processor that executes a program and controls other elements of the server 10. The memory 152 is a main storage device that functions as a work area when the CPU 151 executes a program. The storage 153 is an auxiliary storage device that stores various programs and data. The communication IF 154 is an interface that communicates with other devices in accordance with a predetermined communication standard.

In this example, the storage 153 stores a program (hereinafter, "server program") that causes a computer device to function as the server 10 in the vital data providing system 1. When the CPU 151 is executing the server program, the CPU 151 is an example of the receiving unit 101, the identifying unit 102, the writing unit 104, the clustering unit 105, the receiving unit 106, the extracting unit 107, the output unit 108, the authentication unit 109, and the charge calculation unit 110. In addition, at least one of the memory 152 and the storage 153 is an example of the storage unit 103.

Although detailed description is omitted, the external system 2 and the external system 3 also include, for example, a general-purpose computer device having a CPU, a memory, a storage device, and a communication interface (IF). The user terminal 20 is a general-purpose computer device used by a user; and may be, for example, a smartphone, a tablet terminal, or a personal computer. In the external system 2, the external system 3, and the user terminal 20, a program that causes a computer device to function as a client in the vital data providing system 1 (hereinafter, "client program") is stored. By executing the client program in each device, the functions pertaining to the processes described below are implemented. The client program executed in the external system 2 and external system 3 (providers) and the client program executed in the user terminal 20 (subjects) may be different from each other.

2. Operation

Prior to explaining the operation, a configuration of the vital data providing system 1 will be described. In this example, a business operator (hereinafter, "Business Operator A") provides a vital data recording service (hereinafter, "Service A") using the external system 2. The sensor used to record vital data in Service A is, for example, a wristwatch-type device that functions as an activity meter and measures a subject's steps and pulse. The subject, for example, wears the sensor throughout a day. The sensor measures the subject's steps and pulse at regular time intervals (e.g., every 10 minutes), and stores the measurements together with time stamps. The subject connects the sensor to a relay device (not shown) at a desired timing and transfers the vital data to the relay device. The relay device is, for example, a personal computer, which is connected to the Internet. The subject has registered for service A, and logs into service A from the relay device and uploads his/her vital data to the server 10. The user (subject) who has logged into service A can view or download his/her vital data, but cannot view or download vital data of others.

The business operator A and another business operator (hereinafter, "Business operator B") provide a vital data recording service (hereinafter, "Service B") using the external system 3. The sensor used to record vital data in the external system 3 is a sensor that is attached to a substrate such as a paper, for example, which is coated with an enzyme that reacts with specific components in urine. When the urinary organ is wiped with this substrate after urination, the urine reacts with the enzyme, and the sensor outputs a signal corresponding to the specific component. The sensor includes a communication device that communicates with a relay device (e.g., smartphone; not shown), and transmits the measured values to the relay device via the communication device. The relay device that receives the measured values assigns a time stamp to the measured values and uploads them to the server 10. A user (subject) who logs in to Service B can view or download his/her vital data, but cannot view or download the vital data of others.

Service A and Service B are not compatible with each other, and users of Service A cannot use Service A to view vital data of Service B, and users of Service B cannot use Service B to view vital data of Service A.

A business operator (hereinafter, "Business Operator C") provides a service that integrates these multiple services (hereinafter, "Service C"). The operator C manages the server 10. The operator C may be the same as either the service provider A or the service provider B.

In view of the foregoing, operation of the vital data providing system 1 will now be described. The operation of the vital data providing system 1 can be generally divided into two categories: (a) collection of time-series vital data from external systems, utilization of the collected time-series vital data, and (c) provision of time-series vital data to clients. The provision of time-series vital data can be further divided into the provision of data for businesses and the provision of data for subjects (individuals). Each of these operations is described below.

2-1. Storage of Time-Series Vital Data

Figure 5:
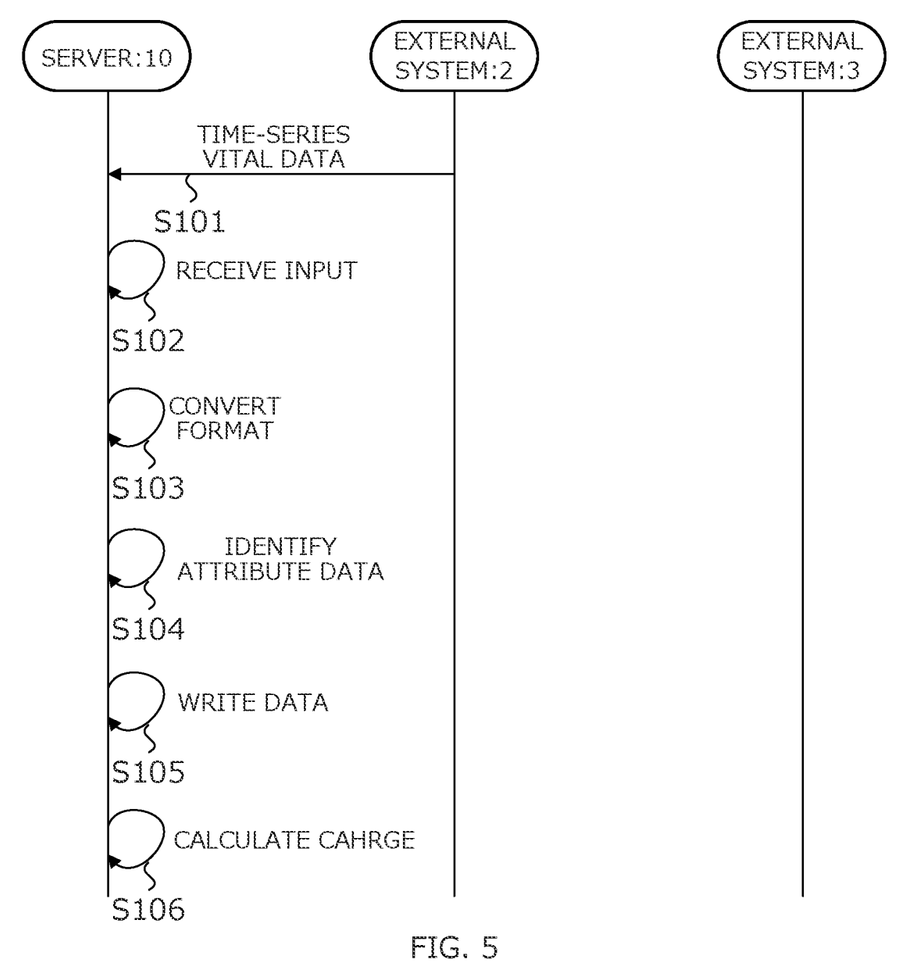
FIG. 5 shows an exemplary sequence chart illustrating the operation of an embodiment.

FIG. 5 shows a sequence chart illustrating the operation of one embodiment of the vital data providing system 1. At a point in time prior to the start of the process shown in FIG. 5, the external system 2 and the external system 3 are operative. The external system 2 and the external system 3 acquire vital data from the first group of subjects and the second group of subjects, respectively, and store the acquired vital data with a time stamp as time-series vital data. In the following, the functional elements such as the receiving unit 101 may be described as the main body of the processing, which means that the hardware elements such as the CPU 151 cooperate with the software elements such as the server program, and execute the processing by controlling other hardware elements as necessary.

At step S101, the external system 2 transmits the time-series vital data to the server 10. The processing at step S101 is triggered by a predetermined event. The event is, for example, an event where a predetermined time has elapsed since a most recent time that the time-series vital data were sent to the server 10. Alternatively, the event is an event in which an amount of untransmitted time-series vital data exceeds a threshold. The external system 2 stores information, for example, a flag that indicates whether the data divided into predetermined units have been transmitted, thereby to identify the untransmitted time-series vital data and the transmitted time-series vital data. The external system 2 identifies the untransmitted time-series vital data by referring to this information, and transmits the data to the server 10. Once the time-series vital data has been transmitted to the server 10, the external system 2 updates the information.

In this example, the external system 2 obtains in advance the consent of each subject to provide the time-series vital data to the service C (operator C). The external system 2 stores the information indicating a presence or absence of such consent in correspondence with the time-series vital data. When transmitting time-series vital data to the server 10, the external system 2 refers to the information indicating the presence or absence of consent, and transmits to the server 10 only the time-series vital data of subjects who have consented to the provision of data.

At step S102, the receiving unit 101 in the server 10 receives the provision (or input) of time-series vital data from the external system 2. The time-series vital data provided by the external system 2 are written in a predetermined format (hereinafter, "the first format"). At step S103, the writing unit 104 converts the format of the time-series vital data provided by the external system 2 from the first format into a standard format. The standard format is a standard data format (or data format) for time-series vital data that are predefined in the server 10. The storage unit 103 stores the first rule for converting the first format to the standard format, and the writing unit 104 converts the format of the time-series vital data received by the receiving unit 101 from the first format to the standard format by referring to the storage unit 103. The storage unit 103 converts the format of the data.

Similarly, the receiving unit 101 receives the input of time-series vital data from the external system 3. The time-series vital data provided by the external system 3 are provided in a predetermined format (hereinafter, "second format"), which is different from that used by the external system 2. The storage unit 103 stores the second rule for converting the second format into the standard format, and the writing unit 104 converts the format of the time-series vital data received by the receiving unit 101 from the second format to the standard format by referring to the storage unit 103.

At step S104, the identifying unit 102 identifies the target attribute data for the target time-series vital data. The target time-series vital data refers to the time-series vital data that is the target among the time-series vital data (group) for which input is received by the receiving unit 101. A target subject refers to a subject of the target time-series vital data. The target attribute data refers to data indicating attributes of the target subject at a time when the time-series vital data is measured. The identifying unit 102 writes the attribute data corresponding to the target time-series vital data to the attribute database 132. In the attribute database 132, the attribute data are recorded in a format that enables reference to changes in the attributes over time.

Various methods can be used to identify the target attribute data. In one example, the external system 2 transmits a data set including time-series vital data and attribute data to the server 10. The external system 2 includes a subject who has a membership of the system and the system is able to obtain the subject's attributes. When the time-series vital data and the attribute data are received as a data set, the identifying unit 102 identifies the attribute data received in the data set with the target time-series vital data as the target attribute data. In another example, when the target time-series vital data are received alone (not in a set with attribute data), the identifying unit 102 determines that the previous attribute is maintained, and the attribute indicated by the latest attribute data registered in the attribute database 132 at that time is determined as maintained. More specifically, when the receiving unit 101 receives the time-series vital data from 0:00 to 23:59 on Dec. 3, 2018, and when there is no attribute data set with the time-series vital data, the identifying unit 102 determines that the attribute indicated by the latest attribute data recorded in the attribute database 132 for the subject (e.g., the attribute as of 23:59 on Dec. 2, 2018), which is indicated by the latest attribute data of the subject recorded in the attribute database 132, is determined as maintained for the period of the target time-series vital data (from 0:00 to 23:59 on Dec. 3, 2018). In yet another example, the target time-series vital data or attribute database 132 includes a link indicating a resource (for example, a network location) where the attribute data is stored. The identifying unit 102 obtains the attribute data from the resource indicated by this link.

The time-series vital data transmitted from the external system 2 may include information specifying a method for identifying the attribute data (e.g., any one of the three examples above). The identifying unit 102 identifies the attribute data using the method specified by this information. Alternatively, a priority order is assigned in advance to these multiple identification methods, and the identifying unit 102 commences with the methods in order of priority, starting with a method assigned a highest priority, and if successful in identifying the attribute data by one method, it moves on to the next process.

Further, the writing unit 104 writes the time-series vital data converted to the standard format to the vital data database 131 (step S105). At this time, in addition to the time-series vital data, the writing unit 104 writes to the vital data database 131 information indicating the correspondence with the attribute data identified in step S104. The information indicating the correspondence with the attribute data includes, for example, at least one of information indicating a location of the attribute data, identification information of the attribute data, and the attribute data itself. In this case, the writing unit 104 may write the time-series vital data and the attribute data to the vital data database 131 and the attribute database 132 in a data structure that shows a correspondence on the time axis.

In writing the time-series vital data to the vital data database 131, the writing unit 104 converts (or assigns) the identification information of the subject. The time-series vital data include identification information to identify the subject (user) from whom the vital data were obtained. Here, in the external system 2 and external system 3, each subject has their own identification information (membership number, etc.; hereinafter, "individual identification information"). If the same person uses both external system 2 and external system 3, it may not be possible to identify the subject from only the identification information given by external system 2 and external system 3. The identification information is converted to deal with this problem. The conversion is a process that enables identity verification. For this process, the identity database 133 is used.

Figure 6:
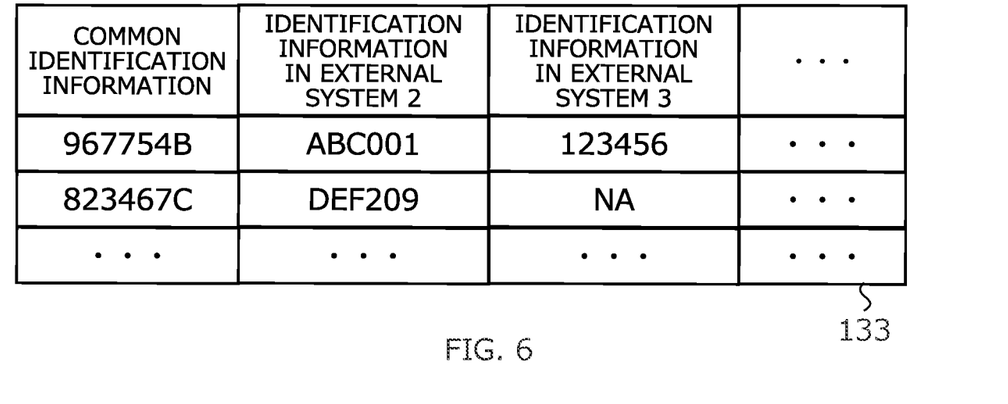
FIG. 6 shows an example of a database of names.

FIG. 6 illustrates an example of the identity database 133. In the identity database 133, identification information in the external system 2, identification information in the external system 3, and identification information in the server 10 are mapped. In the example shown in FIG. 6, for a subject whose identification information "ABC001" is allocated in the external system 2 and whose identification information "123456" is allocated in the external system 3, the server 10 allocates "967754B" as a common identification information (hereinafter, "common identification information"). In addition, another subject who is allocated the identification information "DEF209" in the external system 2 is not registered in the external system 3 (represented as "NA" in the figure), and "823467C" is allocated as the common identification information to this subject. The identity database 133 is created and updated by the operator of the server 10 using a list of subjects provided by operator A and operator B. Alternatively, when the identity database 133 receives unknown identification information from the external system 2, the identity database 133 may send a query to the external system 2 for the personal information corresponding to the identification information. In response to this query, the external system 2 sends to the server 10 a predetermined number of items of personal information (e.g., telephone number and date of birth) corresponding to the identification information. The server 10 stores a database (not shown) that maps the subject's identification information to some of the personal information, and refers to this database to identify the identification information corresponding to the received personal information. In this example, the writing unit 104 is an example of a conversion unit that converts the individual identification information into common identification information.

The description refers to FIG. 5 again. When the writing of the time-series vital data to the vital data database 131 is completed, the charge calculation unit 110 performs a charge calculation process (at step S106). That is, the charge calculation unit 110 calculates a charge amount for the provision of time-series vital data to be provided to the external system 2. The operator of the server 10 calculated here pays the operator of the external system 2 the calculated charge for providing the time-series vital data.

The calculation of the charge is performed, for example, as follows. In one example, the charge is calculated using a number of subjects, a number of measurements, and an indicator of the quality of the data ("quality indicator") (the simplest example is the product of these). An index indicating a quality of the data is obtained, for example, as follows. In this example, for time-series vital data, there are multiple constraints on the time axis that the time-series vital data must satisfy. These constraints are conditions related to the quality of the time-series vital data. The countermeasure 110, for example, calculates a quality index according to the percentage of these constraint conditions that are satisfied. In one example, these constraints are, for example, as follows (a) (For each subject,) the time duration from the time of the first measurement point to the time of the last measurement point is greater than or equal to a threshold duration. The threshold duration is determined, for example, depending on the cycle of sending time-series vital data from the external system to the server 10. In one example, the threshold duration is half of the cycle. More specifically, if the cycle is 24 hours, the threshold duration is 12 hours.

(b) (For each subject,) the time interval between two adjacent measurement points is less than or equal to a threshold interval. This threshold interval may also be determined depending on a cycle of sending time-series vital data from the external system to the server 10 similarly to (a). The threshold interval in (b) is shorter than the threshold duration in (a).

(c) The number of measurement points per unit time is greater than or equal to a threshold value.

The above threshold duration and other thresholds may be set to multiple levels. For example, for condition (a), the threshold duration may be set to one of six levels: 2 hours, 6 hours, 12 hours, 24 hours, 48 hours, and 96 hours (the longer the threshold duration is, the better the data quality is). For condition (b), the threshold interval may be set to one of five levels: 4 hours, 2 hours, 60 minutes, 30 minutes, and 5 minutes (the shorter the threshold duration is, the better the data quality is). Furthermore, these thresholds may be changed depending on a type of vital data.

With regard to condition (a), for example, if time-series vital data of 100 subjects are provided, and 40 of these subjects satisfy condition (a) and the remaining 60 subjects do not satisfy condition (a), then the quality indicator is calculated as a value corresponding to 40%, which corresponds to a rate at which the constraint conditions are satisfied.

With respect to condition (b), for example, for time-series vital data consisting of 101 measurement points obtained from a subject, if 56 of the 100 intervals between adjacent measurement points satisfy condition (b), and the remaining 44 intervals do not satisfy condition (b), the percentage of constraints satisfied for this subject is 56%. If the average of all the subjects is 55%, the quality index is calculated as a value corresponding to 55%. When taking the average for all subjects, the weighting may be based on the number of measurement points.

The charge calculation unit 110 stores in the storage unit 103 the calculated charge as described above, together with information identifying the time-series vital data that is the subject of the charge. The operator of the server 10 pays the calculated charge to the operator of the external system 2 based on this record.

In this way, time-series vital data from the external system 2 are recorded in the vital data database 131. Although detailed description is omitted, the time-series vital data received from the external system 3 are handled similarly to the external system 2. However, an event that triggers the transmission of time-series vital data to the server 10 and the frequency thereof may differ between the external system 2 and the external system 3.

Although description has been given of an example where the time-series vital data are provided to the server 10 from the external system 2 or 3, the time-series vital data may be sent directly from the user terminal 20 to the server 10. In such a case, authentication may be performed using the time-series vital data as an authentication key, as described in the example of the external system.

2-2. Analysis of Time-Series Vital Data

The clustering unit 105 analyzes the time-series vital data recorded in the vital data database 131. This analysis includes a clustering process for the time-series vital data.

The clustering unit 105 analyzes the relationship between the attributes of the subject and the time-series vital data. Techniques such as artificial intelligence (AI), machine learning, or deep learning may be used to analyze the data. In one example, the clustering unit 105 clusters the time-series vital data (or classifies the time-series vital data into a plurality of clusters). In this case, the clustering unit 105 is an example of a clustering unit. In clustering, the time-series vital data of each subject may be used as is, or statistical values (such as mean, maximum, or minimum values) of the time-series vital data of each subject may be used. In one example, clustering is performed for each type of time-series vital data (e.g., the clustering is performed separately for uric acid and oxalic acid). The clustering unit 105 may also perform clustering for a particular type of time-series vital data, and the clustering unit 105 may assign the results of this clustering in a format that can be referenced in other types of time-series vital data. In one example, the clustering unit 105 stores in the vital data database 131 information indicating the classification obtained from the clustering result and corresponding to the identification information of the subject. Alternatively, the clustering unit 105 may cluster the attributes of the subject.

The clustering unit 105 may also analyze attributes that affect particular time-series vital data. More specifically, the clustering unit 105 may analyze a correlation between markers of lung cancer and smoking history, or a correlation between exercise history and urinary sugar. In this way, the clustering unit 105 can obtain, from the accumulated time-series vital data, information indicating a relationship between vital data and subject attributes. The clustering unit 105 can further identify, from this information, subjects having attributes that make them susceptible to a particular disease.

In another example, the clustering unit 105 may detect abnormalities in time-series vital data of a particular subject by contrasting the time-series vital data of that subject with time-series vital data of a group of other subjects having the same or corresponding attributes as that subject. For example, the clustering unit 105 may detect an event such as a uric acid level of a subject being significantly higher than uric acid levels of other subjects in the same age group and gender.

In yet another example, the clustering unit 105 may detect abnormal changes or signs thereof from the temporal changes of the measured values in the time-series vital data of a particular subject. For example, the clustering unit 105 detects abnormal changes or signs of abnormal changes when the measured value of oxalic acid suddenly rises to about 40 for a certain subject, while the measured value of oxalic acid has been hovering around 10 for the last two years.

The clustering unit 105 records the information obtained from any of the above analyses in the vital data database 131 or another database. The clustering unit 105 may also output this information to other devices, either on request or automatically. For example, the output destination of this information may be the external system 2, the external system 3, the user terminal 20, or other devices.

2-3. Provision of Time-Series Vital Data
2-3-1. For External Systems

Figure 7:
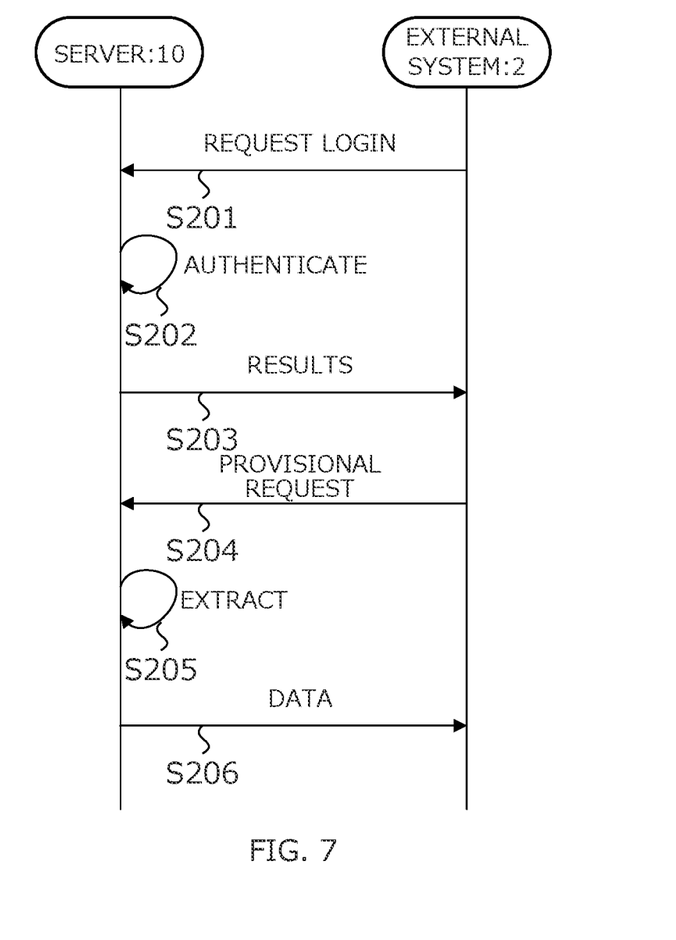
FIG. 7 shows an exemplary operation for providing time-series vital data for external systems.

FIG. 7 is an exemplary flowchart illustrating the operation for providing time-series vital data for an external system. This section describes an example in which the external system 2 acquires time-series vital data of one or more subjects, including subjects other than the user of the external system 2. The external system 2 acquires such time-series vital data, for example, in order to provide statistics on time-series vital data to the user of the external system 2.

In step S201, the external system 2 sends a login request to the server 10. The login request includes, for example, identification information of the external system 2 (for example, contract ID, etc.) and an authentication key. The authentication key is, for example, a password. The identification information and password of the external system 2 are provided, for example, by the operator of the server 10. Upon receiving the login request, the authentication unit 109 of the server 10 authenticates (at step S202) whether the paired identification information and authentication key included in the login request are valid.

In another example, the authentication key includes at least part of the time-series vital data previously obtained by the external system 2 from the subject. This time-series vital data are a part of the time-series vital data that have already been transmitted to the server 10 (recorded in the vital data database 131). The authentication unit 109 of the server 10 checks the time-series vital data included in the received authentication key against the data in the vital data database 131. If it is determined that the same data is recorded in this verification, the authentication unit 109 authenticates the login request. If it is determined that the same data is not recorded, the authentication unit 109 does not authenticate this login request. This technology is described in more detail below.

Figure 8:
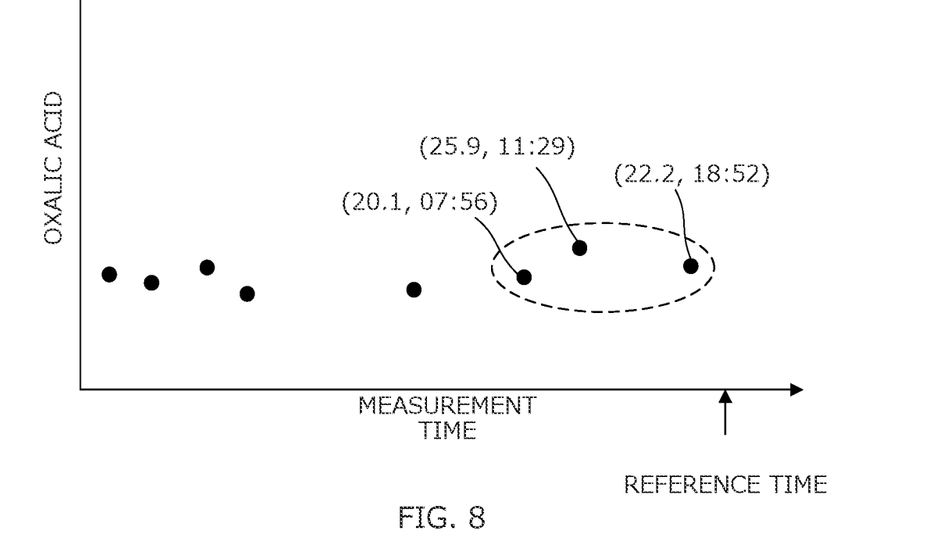
FIG. 8 shows an example of time-series vital data of a subject.

FIG. 8 shows an example of time-series vital data of a subject. The horizontal axis of this figure shows the time of measurement, and the vertical axis shows the measured value (oxalic acid in this example). As described in FIG. 3, the time-series vital data are based on a set of measured values and a time stamp. Since the vital data can be measured at any given time, the arrangement of the set of measurements and time stamps is unique for that subject. For example, referring to a predetermined number (e.g., three sets) of data from a certain reference time (e.g., the current time) (the dashed line in the figure), the set of (measurement value, timestamp) is:

(20.1, 27/11/2018 07:56);
(25.9, 11/27/2018, 11:29); and
(22.2, 11/27/2018 18:52).

An array of the above three sets of data is obtained. The probability that the sequence of these three sets of data is unique to the subject is high. The probability becomes higher when the number of data sets to be acquired is increased. In addition, the sequence of only the measurements from the above example (20.1, 25.9, 22.2) also has a high probability of being unique to that subject. Alternatively, the sequence from the above example where only the time stamps are extracted also has a high probability of being unique to that subject. Therefore, a part of the time-series vital data can be used as an authentication key. Here, "part of the time-series vital data" refers to both a part of the set of measurements and time stamps (first example) and a part of only one of the measurements and time stamps (second and third examples).

According to this method, the larger the number of measurement points, the higher the probability that the data sequence will be unique, i.e., the stronger the security. However, when the number of measurement points is small, such as at the initial stage of taking time-series vital data, security is inevitably weaker. To address this problem, in the example of using a part of the time-series vital data as an authentication key, this "part" may be switched responsive to a trigger. The switching trigger may be, for example, a time of day of access or required security strength. The target of the switch can be a number of subjects, a type of vital data, or the content of the data set. For example, if the number of measurement points in the time-series vital data used for the authentication key is less than a threshold, the set of measurement values and time stamps may be used as the authentication key; if the number of measurement points is greater than the threshold, only one of the measurement values and time stamps may be used as the authentication key. Alternatively, multiple types of vital data (e.g., uric acid and oxalic acid) may be used as the authentication key when the number of measurement points is less than the threshold, and fewer types of vital data (e.g., only uric acid) may be used as the authentication key when the number of measurement points is greater than the threshold.

According to this example, the authentication key will be updated at a high frequency (for example, every time new time-series vital data is entered), thus strengthening security.

The description refers to FIG. 7 again. At step S203, the server 10 sends the result of the processing for the login request (authentication success or authentication failure) to the external system 2, which is the sender of the login request. If the notification of successful authentication is received, the external system 2 sends (at step S204) a request for provision of time-series vital data to the server 10. This provision request includes information for refining the time-series vital data, such as a type of vital data (e.g., uric acid and urinary glucose), attributes of the subject (e.g., male in his 40s), a time period (e.g., two years from 2017 to 2018), a provider of the vital data (e.g., service A), and information (the aforementioned classification information) identifying at least some of the results of the analysis (e.g., clusters with a large number of lung cancer patients) by the clustering unit 105.

At step S205, the extracting unit 107 of the server 10 extracts from the vital data database 131 data to be narrowed down by the information included in the provision request. In this example, the data to be extracted are not only the time-series vital data provided by the external system 2, but also the time-series vital data provided by all systems including the external system 3 (time-series vital data of all subject groups). The output unit 108 transmits (at step S206) the extracted data to the external system 2, which is the source of the provision request. The charge calculation unit 110 calculates the charge for the time-series vital data transmitted to the external system 2. The charge is calculated, for example, in the same manner as in the method described for step S106 (the index used may be different from that at the time of data input). Alternatively, operator C (or the operator of server 10) may charge for time-series vital data in accordance with a contract with operator A (or the operator of external system 2). The contract may be, for example, for a flat rate of payment or for pay-as-you-go.

Operator C may set restrictions on the time-series vital data that can be provided to service provider A through a contract with service provider A. The restrictions may include at least one of the following: those related to the source of the vital data (e.g., only data from Service A and Service B may be provided), those related to the time of measurement (e.g., only data measured in 2018 may be provided), and those related to the attributes of the subject (e.g., only data from people in their 40s may be provided, only data from people living in the Tohoku region may be provided). At least one of these may be included. In this case, the server 10 stores the information about the contract with the operator A in the storage unit 103. The extracting unit 107 extracts only data matching the restrictions indicated by this information.

The data extracted by the extracting unit 107 may include information indicating the results of analysis by the clustering unit 105 (for example, information indicating the clustering classification).

2-3-2. For Subjects

The operation related to the provision of time-series vital data for subjects is essentially the same as that for businesses. In particular, in this example, using one's own vital data as the authentication key has an advantage in that the subject (user) need not remember a password. However, when a provision request is sent from the user terminal 20 to the server 10, the provision request includes identification information that identifies the user (subject). The identification information may be either identification information for an individual service (service A or service B) or common identification information. The extracting unit 107 extracts, from the vital data database 131, the vital data of the subject identified by the identification information included in the provision request. In addition to the identification information of the subject, the provision request may include information for narrowing down the vital data (e.g., data on uric acid in 2018). The extracting unit 107 extracts the vital data narrowed down by this information from the vital data database 131. At this time, the extracting unit 107 may also extract information indicating the results of analysis by the clustering unit 105. The output unit 108 transmits the extracted data to the user terminal 20, which is the sender of the provision request.

Figure 9:
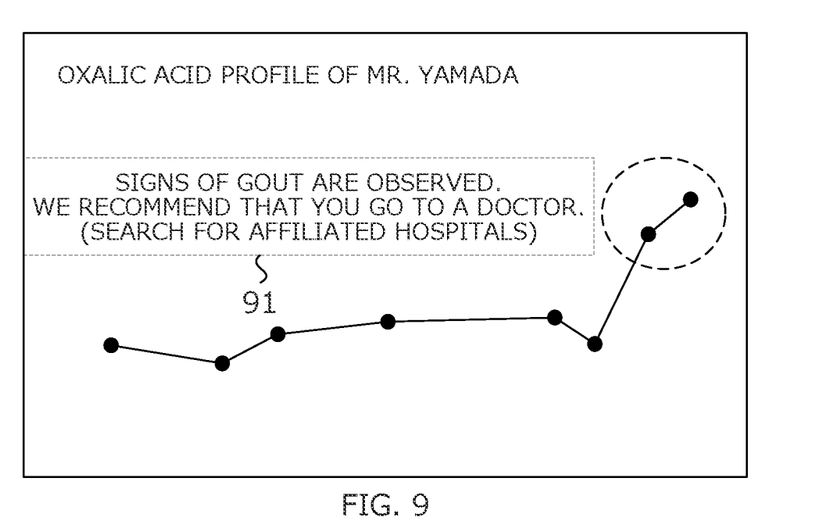
FIG. 9 shows an example of a screen displayed on a user terminal.

FIG. 9 shows an example of a screen displayed on a user terminal 20. This example shows a change in a uric acid level of a subject. In this example, the clustering unit 105 finds that there are signs of gout at the two most recent measurement points, and a message 91 indicating the result is displayed. Specifically, a message "Signs of gout are observed; we recommend that you go to a doctor." is displayed. In addition, below this message, a link to "(search for affiliated hospitals)" is displayed. When the user selects this link, the screen of the user terminal 20 switches to a screen for searching for hospitals affiliated with the vital data providing system 1. The affiliated hospital here is an example of the management entity of the external system. From this screen, the user can search for a hospital that is close to his/her home or workplace, for example. When the user selects a hospital from among the searched hospitals, the screen of the user terminal 20 may further switch to a screen for making an appointment for a medical examination at the selected hospital. Once the appointment for the medical examination is made, the server 10 may transmit the time-series vital data of the subject to the hospital where the appointment is made. Thus, according to this example, signs of illness can be detected earlier, and in subsequent consultations, the vital data prior to the consultation is automatically transmitted to the hospital, allowing the doctor to learn more about the subject's condition.

In another example, the vital data providing system 1 may recommend exercise at a fitness gym. In this case, a search screen for a fitness gym is displayed instead of a search screen for a hospital. The fitness gym is also an example of a management entity of an external system. In yet another example, the vital data providing system 1 may recommend purchase of health food or supplements. In this case, a link to a mail order site for health food or supplements is displayed instead of a search screen for hospitals or fitness gyms. In this way, according to this example, a variety of information can be provided to the subject in accordance with the subject's vital data.

3. Example Modifications

The present invention is not limited to the embodiments described above, and modifications are possible. Some examples of modification are described below. Two or more of the following modifications may be combined, as appropriate.

Some of the functions described as being implemented in the server 10 in the embodiment may be implemented in the client device (external system 2, external system 3, or user terminal 20). For example, the external system 2, the external system 3, or the user terminal 20 may convert the identification information specific to each service into common identification information before transmitting the time-series vital data to the server 10.

Some of the functions described in the embodiments as being implemented in the server 10 may be implemented in other server devices. For example, the clustering unit 105 may be implemented in a different server device to that of the server 10.

The method by which the identifying unit 102 identifies the attribute data is not limited to those illustrated in the embodiment. For example, the server 10 may include an estimation unit (not shown in the figures) for estimating the attribute data of the subject. If the attribute data of a subject cannot be found by a predetermined method, the estimation unit estimates the attribute of the subject. In one example, the estimation unit estimates the current attributes of the subject from past attribute data of the same subject. In this case, the estimation unit may estimate the attribute data by referring to a time variation of the vital data correlated with the attribute data. In another example, the estimation unit may estimate an attribute of the target subject from the attribute data of other subjects belonging to the same cluster as the target subject in the analysis results of the clustering unit 105. In this case, the clustering is based on a particular type of time-series vital data.

The attribute data is not limited to the data illustrated in the embodiments. For example, some of the data acquired as time-series vital data may be used as attribute data for another type of time-series vital data.

In a case that a part of the time-series vital data is used as an authentication key for access to the server 10, information (index information) for identifying a "part" used as an authentication key from a group of time-series vital data may be sent from the device from which the request is sent to the server 10. The index information may include, for example, subject identification information that identifies one subject from among a plurality of subjects. Alternatively, the index information may include time period information that specifies the time period during which the time-series vital data was measured. According to this example, the scope of searching the vital data database 131 in the server 10 can be narrowed down, thereby reducing a load on the server.

Operator A, Operator B, or Operator C may grant a benefit to the provider of the vital data. In this case, each business may change the benefits according to the quality of the data provided. In other words, a higher benefit may be given to subjects who provide high-quality data. The quality of the data is evaluated using the same method that used for the quality index at step S106, for example.

When providing vital data according to a request for provision from the user terminal 20, the extracting unit 107 may thin out the measurement points according to the time length of the vital data provided. For example, when vital data for 10 years is requested, the extracting unit 107 thins out the number of data points for the unit period to ¹⁄₁₀ compared to a case where data for one year is requested.

The sequence chart in the embodiment is merely an example, and the operation of the vital data providing system 1 is not limited thereto. For example, the processing order may be different from that described in the embodiment.

The programs to be executed by the various computer devices in the embodiment may be provided in a state recorded on a non-transitory storage medium (CD-ROM, flash memory, etc.).

What is claimed is:

1. A server comprising:
   an input receiving unit that receives input of a first type of time-series vital data from a first system for collecting the first type of time-series vital data from a first group of humans;
   an identifying unit that identifies attribute data indicating an attribute of a human of the first group of humans at a time when the time-series vital data was measured from the human, for time-series vital data that are a target among the time-series vital data input of which is received by the input receiving unit, the attribute including non-vital time series data of the human;
   a writing unit that writes the time-series vital data, the input of which is received by the input receiving unit, into a vital data database together with information indicating a correspondence relationship with the attribute data identified by the identifying unit;
   a clustering unit that clusters the time-series vital data recorded in the vital data database based on the attribute data;
   a request receiving unit that receives a request for providing data, the request including classification information that specifies the cluster by the clustering unit;
   an extracting unit that extracts the time-series vital data belonging to the cluster specified by the classification information from the vital data database, the time-series vital data extracted by the extracting unit coming from ore the none human, the more that one human belonging to the cluster; and
   an output unit that outputs the time-series vital data from the more than one human extracted by the extracting unit to a device specified by the request, the time-series vital data output by the output unit not including personal information of the more than one human, the personal information being in form on to identify a person,
   wherein the time series vital data shows at least one of blood pressure, heart rate, body temperature, oxygen saturation concentration in blood, body weight, blood glucose, urine glucose, uric acid in blood or urine, oxalic acid, specific gravity, protein, urobilinogen, pH, serum iron, inflammation markers, creatinine, cholesterol ketones, cancer markers, *H. pylori*, steps, pulse, acceleration, location, calories consumed, outside temperature, outside humidity, and amount of sleep measured from a body of the human.

2. The server according to claim 1, wherein the vital data database stores the attribute data in a format that allows reference to changes in the attribute data over time.

3. The server according to claim 1, further comprising: an estimation unit that estimates the attributes of the human.

4. The server according to claim 1, wherein the output unit transmits to the device, along with the extracted time-series vital data, classification information indicating clusters into which the time-series vital data are classified by the clustering unit.

5. The server according to claim 1, wherein the identifying unit identifies the attribute data based on links corresponding to the time-series vital data.

6. The server according to claim 1, wherein the request includes an authentication key to authenticate a device;
the server further comprises an authentication unit to authenticate the device using the authentication key included in the request, wherein
when the device is authenticated by the authentication unit, the output unit outputs time-series vital data selected in accordance with the request.

7. The server according to claim 6, wherein
the authentication key includes at least one of timestamps and measurements of at least two data points of time-series vital data previously acquired at the device; and
the authentication unit performs authentication by matching the authentication key with the time-series vital data stored in the vital data database.

8. The server according to claim 7, wherein
if the number of data points in the time-series vital data included in the authentication key is less than a threshold value, the authentication key includes both the time stamps and the measurement values of the at least two data points, and
if the number of data points in the time-series vital data included in the authentication key is greater than the threshold value, the authentication key includes only one of the timestamps and the measurement values of the at least two data points.

9. The server according to claim 7, wherein
the authentication key includes index information for identifying data points from the time-series vital data stored by the device, and
the authentication unit performs the authentication by matching the authentication key with the data points identified by the index information among the time-series vital data stored in the vital data database.

10. The server according to claim 9, wherein
the index information includes human identification information that identifies one human from among a plurality of humans, and
the authentication unit performs the authentication by matching the authentication key with the data points included in the time-series vital data of the one human from among the time-series vital data stored in the vital data database.

11. The server according to claim 1, wherein
the input receiving unit receives input of a second type of time-series vital data from a second system that collects the second type of time-series vital data from a second group of humans,
the identifying unit identifies the attribute data indicating the attribute of the human at the time when the time-series vital data was measured, for the time-series vital data that is the human among the second type of time-series vital data, and
the writing unit writes the second type time-series vital data to the vital data database together with information indicating the correspondence with the attribute data identified by the identifying unit.

12. The server according to claim 11, further comprising:
a conversion unit that converts individual identification information into common identification information commonly used in the vital data database if the time-series vital data received by the input receiving unit include individual identification information that identifies the human of the time-series vital data, the individual identification information being individually assigned in the first system or the second system, wherein
the vital data database stores the common identification information as information to identify the human.

13. The server according to claim 11, wherein
the clustering unit classifies the second type of time-series vital data based on the first type of time-series vital data from among multiple types of time-series vital data.

14. The server according to claim 11, wherein
the input receiving unit receives vital data written in a first format from the first system, and receives vital data written in a second format from the second system,
the vital data database stores a first rule for converting the vital data in the first format to the vital data in a standard format, and a second rule for converting the vital data in the second format to the vital data in the standard format, and
the writing unit writes the data converted from the vital data received by the input receiving unit to the standard format to the vital data database.

15. The server according to claim 11, wherein
the vital data database stores multiple types of time-series vital data,
the request includes information to select at least some of the multiple types, and
the output unit transmits to the device the type of vital data selected in accordance with the request, the type of vital data being selected from among the vital data of all human groups including the first and second human groups, the vital data being stored in the vital data database.

16. The server according to claim 1, wherein
the request includes time period information to narrow down a time period,
the output unit transmits to the device vital data measured during a limited time period in accordance with the request, the transmitted vital data being selected from the time-series vital data stored in the vital data database.

17. The server according to claim 1, further comprising
a calculation unit that calculates a charge for the time-series vital data received by the input receiving unit.

18. The server according to claim 17, wherein
constraint conditions on a time axis to be satisfied by the time-series vital data are set, and the calculation unit calculates the charge in accordance with a percentage of the data received by the input receiving unit that satisfies constraint conditions.

19. An information processing method comprising:
receiving an input of a first type of time-series vital data from a first system that collects the first type time-series vital data from a first group of humans;
identifying attribute data indicating an attribute of a human of the first group of humans at a time when the time-series vital data was measured from the human, for the time-series vital data that is a target among the time-series vital data for which the input was received, the attribute including non-vital time series data of the human;
writing the input time-series vital data into a vital data database, together with information indicating a correspondence with the identified attribute data;
clustering the time-series vital data recorded in the vital data database based on the attribute data;
receiving a request to provide data, the request including classification information specifying cluster by the clustering;
extracting the time-series vital data belonging to a cluster specified by the classification information from the vital data database, the extracted time-series vital data coming from more than one human, the more than one human belonging to the cluster; and
outputting the extracted time-series vital data from the more than one human to a device specified by the request, the output time-series vital data not including personal information of the more than one human, the personal information being information to identify a person, wherein the time series vital data shows at least one of blood pressure, heart rate, body temperature, oxygen saturation concentration in blood, body weight, blood glucose, urine glucose, uric acid in blood or urine, oxalic acid, specific gravity, protein, urobilinogen, pH, serum iron, inflammation markers, creatinine, cholesterol ketones, cancer markers, *H. pylori*, steps, pulse, acceleration, location, calories consumed, outside temperature, outside humidity, and amount of sleep measured from a body of the human.

20. A non-transitory computer-readable medium storing a program for causing a computer to execute a process by a processor so as to perform the steps of:

receiving an input of a first type of time-series vital data from a first system that collects the first type time-series vital data from a first group of humans;

identifying attribute data indicating an attribute of a human of the first group of humans at a time when the time-series vital data was measured from the human, for the time-series vital data that is the target among the time-series vital data for which the input was received, the attribute information including non-vital series data of the human;

writing the input time-series vital data into a vital data database, together with information indicating a correspondence with the identified attribute data;

clustering the time-series vital data recorded in the vital data database based on the attribute data;

receiving a request to provide data, the request including classification information specifying a cluster by the clustering;

extracting the time-series vital data belonging to a cluster specified by the classification information from the vital data database, the extracted time-series vital data coming from more than one human, the more than one human belonging to the cluster; and outputting the extracted time-series vital data from the more than one human to a device specified by the request, the output time-series vital data not including personal information of the more than one human, the personal information being information to identify a person, wherein the time series vital data shows at least one of blood pressure, heart rate, body temperature, oxygen saturation concentration in blood, body weight, blood glucose, urine glucose, uric acid in blood or urine, oxalic acid, specific gravity, protein, urobilinogen, pH, serum iron, inflammation markers, creatinine, cholesterol ketones, cancer markers, *H. pylori*, steps, pulse, acceleration, location, calories consumed, outside temperature, outside humidity, and amount of sleep measured from a body of the human.

* * * * *